United States Patent [19]

Lantos

[11] 4,096,248

[45] Jun. 20, 1978

[54] SULFONYL CONTAINING ORGANIC GOLD GLYCOSIDE COMPOUNDS AND METHOD OF USE

[75] Inventor: Ivan Lantos, Blackwood, N.J.

[73] Assignee: SmithKline Corporation, Philadelphia, Pa.

[21] Appl. No.: 769,145

[22] Filed: Feb. 16, 1977

[51] Int. Cl.$^2$ .................... A61K 31/70; C07H 5/10
[52] U.S. Cl. ........................... 424/180; 536/4; 536/117; 536/121; 536/122
[58] Field of Search ............... 536/117, 118, 121, 122; 424/180

[56] References Cited

U.S. PATENT DOCUMENTS 3,635,945  1/1972  Nemeth et al. .................... 536/4

*Primary Examiner*—Johnnie R. Brown
*Attorney, Agent, or Firm*—William H. Edgerton

[57] ABSTRACT

A new series of lower alkyl sulfonyl esters of S-tri-lower-alkylphosphinegold 1-thio-β-D-glucopyranosides has been prepared and found to have anti-arthritic activity and, in particular, are of use in treating rheumatoid arthritis.

7 Claims, No Drawings

SULFONYL CONTAINING ORGANIC GOLD GLYCOSIDE COMPOUNDS AND METHOD OF USE

This invention relates to a new series of organic gold compounds whose structures are characterized in that they are tetra-O-lower alkylsulfonyl esters of S-tri-loweralkylphosphinegold(I) 1-thio-β-D-glucopyranosides. These new compounds have anti-arthritic activity and, in particular, are of use in the treatment of rheumatoid arthritis.

It is known in the prior art that certain gold containing glucopyranosides have oral anti-arthritic activity (U.S. Pat. No. 3,635,945). The compounds of this prior art patent are limited to the 1-thio-β-D-glucopyranoside phosphinegold complexes in the tetrahydroxy or tetra-O-acetyl form. There is no disclosure in this patent of any tetra-O-lower alkylsulfonyl derivatives of the glucopyranoside phosphinegold compounds and no suggestion that such sulfonyl ester derivatives would have any anti-arthritic activity.

The compounds of this invention are the tetra-O-lower alkylsulfonyl esters of S-tri-lower-alkylphosphinegold(I) 1-thio-β-D-glucopyranoside. They are illustrated by the following structural formula:

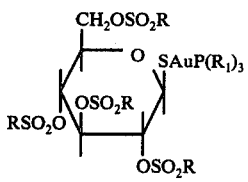

I in which:

R is lower alkyl of 1–4 carbon atoms preferably methyl; and $R_1$ is lower alkyl of 1–4 cabon atoms preferably ethyl.

The compounds of this invention are prepared by reacting a 1-thio-2,3,4,6-tetra-O-lower alkylsulfonyl-β-D-glucopyranose in the form of its silver salt with a halo (tri-lower-alkylphosphine)gold(I) in an inert organic solvent mixture in which the reactants are soluble such as tetrahydrofuran. The reaction is often run at ambient temperatures for up to 2–8 hours. The product is isolated from the reaction mixture by methods common in the art.

The starting material silver salt of 1-thio-2,3,4,6-tetra-O-alkylsulfonyl glucopyranoses are prepared by reacting the corresponding S-trityl derivative with silver nitrate in an inert solvent in which the reactants are soluble such as methanol:methylene chloride.

The S-trityl intermediates are prepared in turn by acylation of the S-trityl-1-thioglucopyranose using a lower alkylsulfonyl chloride or bromide in pyridine.

The halo(tri-lower-alkylphosphine)gold(I) compounds which are the other starting materials are prepared as described in U.S. Pat. No. 3,635,945.

The compounds of this invention are useful in treatment of arthritis. This activity is demonstrated by the following test procedure.

Inhibition of adjuvant induced polyarthritis in rats, as measured by reduction of rat paw edema, is produced by compounds of this invention such as S-triethylphosphinegold(I) 2,3,4,6-tetra-O-methylsulfonyl-1-thio-β-D-glucopyranose at daily oral doses of about 20 mg/kg (calculated on gold content). In this test procedure, adjuvant arthritis in rats is produced by a single intradermal injection of 0.75 mg of Mycobacterium butyricum suspended in white paraffin oil into the left hindpaw footpad. The injected paw becomes inflamed (increased volume) and reaches maximal size within three to five days (primary lesion). The animals exhibit a decrease in body weight gain during the initial period. The adjuvant arthritis (secondary lesion) occurs after approximately ten days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Anti-arthritic activity is shown by the ability to inhibit the development of either primary or secondary lesions of adjuvant arthritis. Auranofin which is a clinically effective anti-arthritic is active in test procedure at doses of from 10–20 mg/kg orally.

The compounds of this invention are administered in conventional dosage forms prepared by combining a compound of Formula I in a nontoxic amount sufficient to produce anti-arthritic activity with standard pharmaceutical carriers according to conventional procedures. These procedures may involve mixing, granulating and compressing or dissolving the ingredients as appropriate to the desired preparation. The resulting pharmaceutical compositions are also objects of this invention. Oral dosage forms are preferred.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampule or nonaqueous liquid suspension.

Preferably, each dosage unit will contain the active ingredient in an amount of from about 1 mg to about 10 mg.

The method of producing anti-arthritic activity by administering internally to an animal in need of treatment a compound of Formula I is also an object of this invention. The compound of Formula I is administered in an amount sufficient to produce anti-arthritic activity but have no limiting side effects. The route of administration is preferably oral. The daily dosage regimen will be preferably from about 1 mg to about 12 mg most often in one or two oral doses daily. When the method is carried out as described above, anti-arthritic activity is produced in a subject with arthritic symptoms, for example in humans or in domestic animals such as dogs.

One skilled in the art will recognize that in determining the amounts of active ingredient in the claimed compositions and used in the claimed methods, the activity of the chemical ingredient as well as the size and condition of the host animal must be considered.

The amounts given above are calculated for the average human subject.

The term "lower alkyl" where used herein denote groups having preferably 1–4 carbon atoms preferably methyl.

The following examples are not limiting but are illustrative of the invention. Any melting points are in degrees Centigrade.

EXAMPLE 1

Preparation of S-trityl-2,3,4,6-tetra-O-acetyl-1-thio-β-D-glucopyranose 2,3,4,6-Tetra-O-acetyl-thio-β-D-glucopyranose, obtained from the hydrolysis of 29 g of the 1-isothiouronium compound as in R. L. Whistler and M. L. Wolfrom, eds, "Methods in Carbohydrate Chemistry", Vol. II, pg. 436, Academic Press (1963), was dissolved in 250 ml of chloroform then cooled to 0°–5° in a ice-bath. Anhydrous pyridine (20ml) was added, followed by 27.9 g of triphenylmethyl (trityl) chloride. The mixture was stirred overnight at ambient temperature. The organic solution was extracted with dilute hydrochloric acid (2x), washed with 5% aqueous sodium carbonate solution and with brine. The chloroform solution was then dried and evaporated under reduced pressure to obtain an oil which crystallized from ether. The product was then recrystallized from benzene-cyclohexane to obtain an analytical sample, m.p. 177.5°–179.5°, yield: 12.0 g.

Preparation of S-trityl-2,3,4,6-tetra-O-methylsulfonyl-thio-β-D-glucopyranose The above prepared tetraacetyl compound (21.0 g) was suspended in 90 ml of methanol. The suspension was cooled to −15° and a solution of sodium methoxide, prepared from 0.21 g of sodium in 75 ml of methanol, was added. Hydrolysis of the acetate was carried out by stirring at room temperature for 1 hour. The solution was concentrated under reduced pressure to obtain a solid residue. The solid was triturated with water then taken up in chloroform. The milky chloroform solution was filtered, evaporated to leave a solid which was dried overnight with azeotropic distillation in benzene. Further evaporation of the solvent and drying in vacuo yielded 16.3 of S-trityl-1-thio-β-D-glucopyranose.

This hydroxy compound (3.6 g) was dissolved in 50 ml dry pyridine, cooled to 0° while 5 ml (7.5 g) of methylsulfonyl (mesyl) chloride was added. The solution was placed in the refrigerator for 22 hours until a tlc test showed only traces of starting material or partially reacted products remaining. The solvent was removed at reduced pressure. The only residue was dissolved in chloroform (200 ml) and was washed with dil. hydrochloric acid and brine. Evaporating the dried organic extract yielded a crude product, 3.65 g, which was chromatographed over a silica dry-column using 20% ethyl acetate-80% chloroform eluent. Pure product (2.75 g) was obtaind from ether.

Preparation of the Silver Salt

S-Trityl-2,3,4,6-tetra-O-methylsulfonyl-1-thio-β-D-glucopyranose (1.8 g) was dissolved in 6 ml of methylene chloride and 12 ml methanol and 0.41 g of granular silver nitrate was added. The mixture was allowed to stand overnight at room temperature yielding 1.39 g of a solid precipitate, the required silver salt, which was filtered, dried and analyzed for the molecular composition.

$C_{10}H_{19}O_{13}S_5Ag$: Calculated: 19.52% C; 3.11% H. Found: 19.68% C; 3.16% H.

Preparation of S-triethylphosphinegold(I) 2,3,4,6-tetra-O-methylsulfonyl-1-β-D-glucopyranoside The silver salt (2.0 g) prepared above was dissolved in 200 ml of tetrahydrofuran and 1.12 g of triethylphosphinylgold(I) chloride was added. The progress of the reaction was monitored with tlc and after completion, 5–7 hours, the silver chloride precipitate was filtered and the solution was evaporated at reduced pressure to yield the analytically pure tetramethylsulfonyl (tetramesyl) compound named above.

$C_{16}H_{34}O_{13}PS_5Au$: Calculated: 23.36% C; 4.17% H. Found: 23.36% C; 4.05% H.

IR(Nujol cm$^{-1}$): 1361 and 1173 (strong, $CH_3SO_2$), 1042 (m, C—O), 769 (broad, PEt$_3$)

NMR(CDCl$_3$, δ): 7.0 (broad, 1H), 5.70–4.5 (complex multiplets, 6H), 3.41–3.1 (overlapping singlets, 4CH$_3$SO$_2$), 2.25–0.9 (multiplet, PEt$_3$).

EXAMPLE 2

Substituting equivalent amounts of chloro(triisopropylphosphine)gold(I), chloro(tributylphosphine)gold(I) or chloro(trimethylphosphine)gold(I) in the final step of Example 1 gives S-triisopropylphosphinegold(I), 2,3,4,6-tetra-O-mesyl-1-thioβ-D-glucopyranoside, S-tributylphosphinegold(I) 2,3,4,6-tetra-O-mesyl-1-thio-β-D-glucopyranoside or S-trimethylphosphinegold(I) 2,3,4,6-tetra-O-mesyl-1-thio-β-D-glycopyranoside.

EXAMPLE 3

Substituting an equivalent amount of S-trityl 2,3,4,6-tetra-O-ethylsulfonyl-1-thio-β-D-glucopyranose in Example 1 (prepared using ethylsulfonyl chloride in place of the mesyl chloride in Example 1) gives S-triethylphosphinegold(I) 2,3,4,6-tetra-O-ethylsulfonyl-1-thio-β-D-glucopyranoside. Substituting an equivalent amount of S-trityl-2,3,4,6-tetra-O-isopropylsulfonyl-1-thio-β-D-glucopyranose (using isopropylsulfonyl chloride) gives S-triethylphosphine(I) 2,3,4,6-tetra-O-isopropylsulfonyl-1-thio-β-D-glucopyranoside.

EXAMPLE 4

| Ingredients | Amounts |
| --- | --- |
| S-triethylphosphinegold(I) 2,3,4,6-tetra-O-mesyl-1-thio-β-D-glucopyranoside | 5 mg |
| magnesium stearate | 5 mg |
| lactose | 140 mg |

The above ingredients are mixed, screened and filled into a hard gelatin capsule. The capsule is administered orally twice daily to a human subject having arthritis.

EXAMPLE 5

| Ingredients | Amounts |
| --- | --- |
| S-triethylphosphinegold(I) 2,3,4,6-tetra-O-mesyl-1-thio-β-D-glucopyranoside | 6 mg |
| Peanut Oil | 94 mg |

The ingredients are mixed and filled into a soft gelatin capsule which is administered orally to a subject in need of treatment once a day. If no improvement is noted, the dose is increased until either improvement is noted or toxic effects preclude further increase in dosage.

What is claimed is:

1. A chemical compound of the formula:

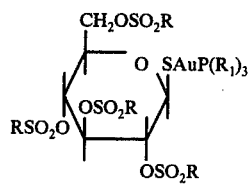

in which:

R and $R_1$ are each respectively lower alkyl of 1-4 carbons.

2. A compound of claim 1 in which R is methyl.

3. A compound of claim 2 in which $R_1$ is ethyl.

4. A pharmaceutical composition having anti-arthritic activity, in dosage unit form, comprising a pharmaceutical carrier and an effective amount of a compound of claim 1.

5. A method of producing anti-arthritic activity which comprises administering internally to a subject in need of treatment an effective amount of a compound of claim 1.

6. The method of claim 5 in which the compound is S-triethylphosphinegold(I) 2,3,4,6-tetra-O-methylsulfonyl-1-thio-β-D-glucopyranoside which is administered orally.

7. The method of claim 6 in which the daily dosage is chosen from the range of from 1-12 mg of active ingredient.

* * * * *